(12) United States Patent
Arulkumaran et al.

(10) Patent No.: US 6,423,011 B1
(45) Date of Patent: Jul. 23, 2002

(54) APPARATUS AND METHOD FOR FETAL SCALP BLOOD SAMPLING

(75) Inventors: Sabaratnam Arulkumaran, Derby (GB); Wm. Dean Wallace, Salt Lake City, UT (US)

(73) Assignee: Clinical Innovation Associates, Inc., Murray, UT (US)

( * ) Notice: Subject to any disclaimer, the term of this patent is extended or adjusted under 35 U.S.C. 154(b) by 0 days.

(21) Appl. No.: 09/517,035

(22) Filed: Mar. 2, 2000

(51) Int. Cl.$^7$ .............................................. A61B 5/00
(52) U.S. Cl. ...................................................... 600/576
(58) Field of Search ......................... 600/562, 564–567; 606/167, 170

(56) References Cited

U.S. PATENT DOCUMENTS

| | | |
|---|---|---|
| 3,685,509 A | 8/1972 | Bentall |
| 4,360,016 A | 11/1982 | Sarrine |
| 4,660,570 A | 4/1987 | Dombrowski |

OTHER PUBLICATIONS

Schneider, K.T.M. et al., A Device for Easier Collection of Fetal Scalp Blood, J. Perinat. Med. 11 (1983) (2 pages).
Arulkumaran, S. et al., A New Fetal Scalp Blood Sampling Device, Institute of Obstetrics and Gynaecology, London (1990) (3 pages).
Arulkumaran, S. et al., The Selection of Capillary Tube Diameter for Fetal Scalp Blood Sampling, British Journal of Obstetrics and Gynaecology, Aug. 1990. vol. 97, pp. 744–747.
Drawing Sheets, four (4) pages, Fetal Scalp Blood Sampling Device, Aug. 1990.

Primary Examiner—Max Hindenburg
(74) Attorney, Agent, or Firm—Traskbritt

(57) ABSTRACT

A method and apparatus for collecting blood from a fetal scalp. The apparatus includes an elongated housing containing a longitudinally spring-loaded, sharp-pointed, beveled blade disposed at the distal end thereof which can be advanced against the spring bias from the distal end against the fetal scalp. A groove located on an exterior side surface of the distal end of the housing is sized to receive a capillary tube which is resiliently retained on the housing with its distal end proximate a recessed region at the distal end of the housing. The groove may be oriented parallel to the housing, or at an angle thereto, to enhance visualization of blood pooling in the recessed region filling the capillary tube after an incision in the scalp is made using the blade. A light source may be included in or on the apparatus, or on the interior of an amnioscope with which the apparatus is employed. A method of using the apparatus is also disclosed.

31 Claims, 2 Drawing Sheets

Fig. 1

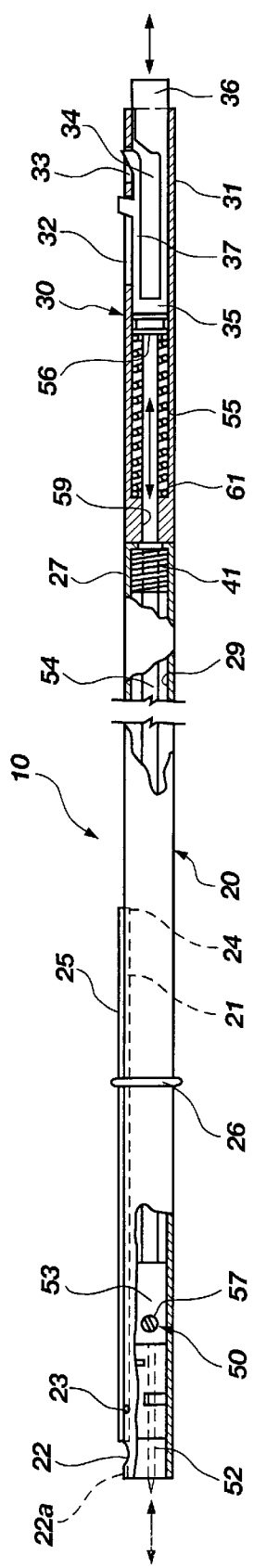
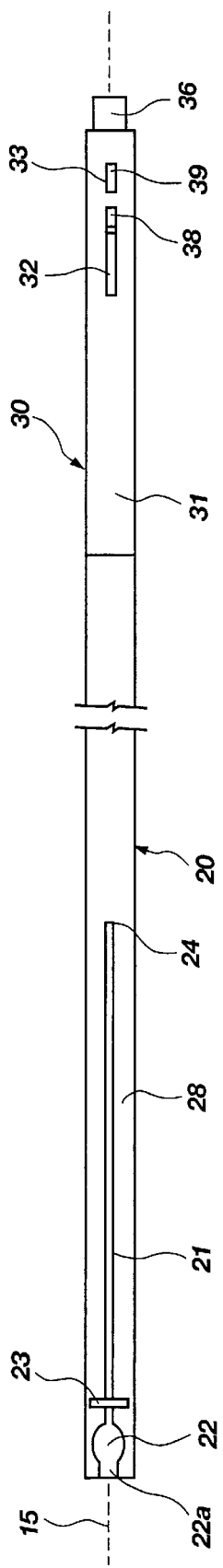
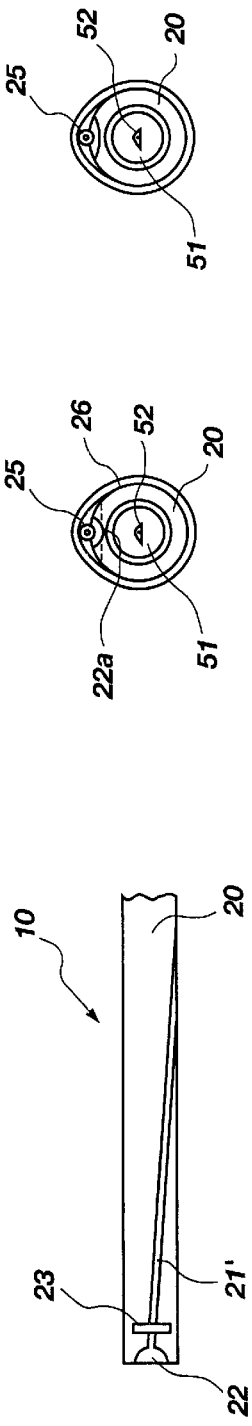
Fig. 1
Fig. 2
Fig. 2A
Fig. 3
Fig. 3A

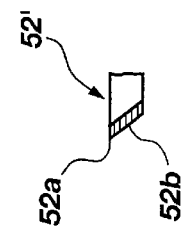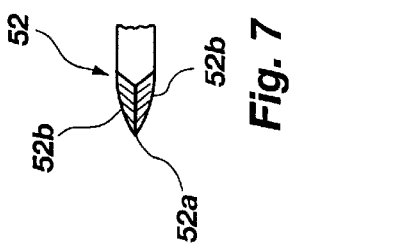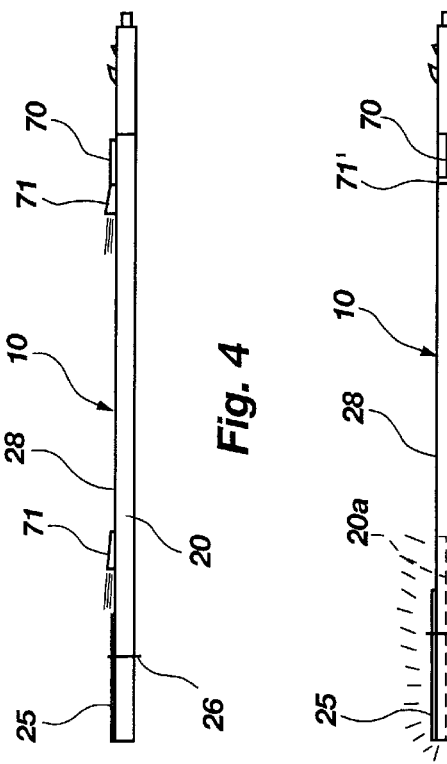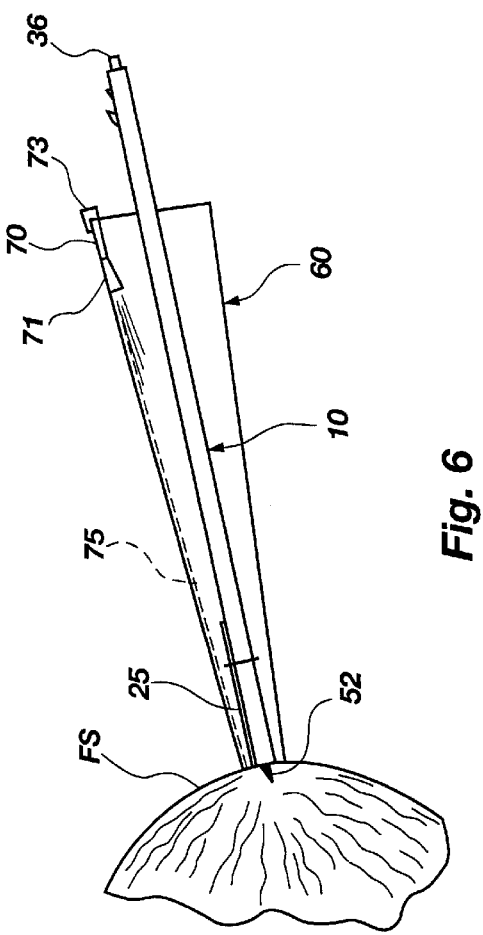

APPARATUS AND METHOD FOR FETAL SCALP BLOOD SAMPLING

BACKGROUND OF THE INVENTION

1. Field of the Invention

This invention relates generally to a blood collection apparatus and a method for using the same. In particular, this invention relates to a blood collection apparatus for making an incision in the scalp of a fetus and collecting blood resulting from the incision in a capillary tube attached to the device in a manner in which the blood being drawn into the capillary tube can be viewed.

2. State of the Art

Collecting blood from an infant during the birthing process is employed extensively when the doctor suspects an infant is not receiving an adequate supply of oxygen due to strangulation of an umbilical chord or premature separation of the placenta. Fetal blood sampling conventionally involves passing an amnioscope through the birth canal and pressing it onto the fetal presentation, creating a "cofferdam seal" between the fetal scalp and a distal end of the amnioscope. A lance, long-handled scalpel, or other similar scalp-puncturing or incising instrument is then introduced through the amnioscope to make an incision. The blade is kept perpendicular to the surface of the scalp, and the puncture or incision achieved by a sudden thrust forward. After the scalp puncture is made, the scalp-puncturing instrument is removed and a long capillary tube, or a short capillary tube at the distal end of a holder, is advanced inside the amnioscope to collect a sample of the blood from that exuding from the scalp. Finally, the sample of blood is transferred from the long capillary tube into a special capillary tube designed for use with blood gas analysis equipment. If a short capillary tube is used, it may be configured for compatibility with blood gas analysis equipment and used directly therewith.

This procedure, however, is relatively time consuming under the circumstances of child birth, and exhibits a high potential for error due to the exchange of multiple instruments. Further, other areas of concern are lack of careful control of the depth of the incision (preferably no deeper than 2.5 mm) and the avoidance of contamination from the transfer of blood from the sampling tube to the analysis tube.

A blood collecting device disclosed in U.S. Pat. No. 4,360,016 to Sarrine addresses some of the problems discussed above by disclosing a single device that performs both the functions of puncturing a fetal scalp and collecting blood resulting from the puncture. In particular, Sarrine discloses a tubular member with a collar at its distal end and a head at its proximal end, the head being spring-biased away from the proximal end and having a catch or tab to hold it against the bias. In addition, at the distal end of the tubular member there is a wedge slidably mounted therein and connected to the head by an intermediate rod, the wedge carrying a lancet blade projecting distally from its distal end. A capillary tube for collecting blood is clipped in a recess in the side of the tubular member with the distal end of the tube located directly underneath the lancet blade and encircled within the collar. In use, the distal end of the tubular member is placed against the fetal scalp, after which the spring-loaded head is depressed, moving the wedge distally a predetermined distance to puncture the fetal scalp. Blood resulting from the puncture is then asserted to pool within the lower portion of the collar, where the blood is drawn by capillary action into the bore of the capillary tube.

However, there are several problems associated with the device disclosed in Sarrine. For example, since the capillary tube is located within a recess in the side of the tubular member and is rotationally disposed at the underside of the tubular member as the device is used, the tubular member obscures any view of the capillary tube so that it is impossible to determine if and when blood is being collected, or when the capillary tube is sufficiently filled without withdrawing the device from the mother. This drawback will often necessitate in reiterating the procedure of puncturing the scalp of the infant until an appropriate blood sample is collected. Further, there is the potential problem of damaging the capillary tube or contaminating the blood sample when extracting the capillary tube from the recess in the tubular member after the blood has been collected because the distal end of the capillary tube is encircled by the collar and the clips holding the tube are located within the recess. In addition, Sarrine does not necessarily place the capillary tube on the device in a position designed to collect blood at the highest efficiency.

BRIEF SUMMARY OF THE INVENTION

In overcoming the deficiencies of the prior art, the present invention provides an apparatus for making an incision in a fetal scalp and efficiently collecting blood emanating from the scalp incision in a capillary tube while facilitating visualization of the tube during the collection process.

In addition, the present invention provides an apparatus for incising the fetal scalp of a design from which the capillary tube can be easily removed from the device to limit potential damage of the capillary tube or contamination of the tube or the blood therein.

The present invention also provides an apparatus on which the capillary tube can be easily and precisely positioned with the tube located and oriented to collect blood efficiently.

The present invention comprises an elongated, substantially tubular housing with a proximal end, a distal end and a bore extending longitudinally therethrough. A plunger which includes a proximal portion extending beyond the proximal end of the housing, which is proximally spring-biased and has associated therewith a catch and a release element, is slidably disposed in the proximal end of the elongated housing, which may comprise a biasing mechanism formed separately from the remainder of the elongated housing. An extension member 54 is secured to the plunger and extends distally within the bore of the elongated housing. A blade assembly is secured within the bore to a distal end of the extension member 54 and is extendable beyond the distal end of the elongated housing responsive to longitudinal pressure applied to the proximal portion of the plunger. A groove is formed in an exterior surface of the elongated housing proximate the distal end to receive a side of a capillary tube placed on the housing and retained thereon with a retention element. The groove may be parallel to the longitudinal axis of the housing, or may be oriented at a small, acute angle thereto so as to provide a three-dimensional perspective and facilitate viewing of blood traveling up the capillary tube.

The groove on the elongated housing exterior includes a recessed, shallowly cupped or spooned region proximate the distal end thereof. Further, the groove is preferably formed to a predetermined length so that when the capillary tube is received within the groove, the distal end of the capillary tube is disposed at a proximal end of the recessed region. Furthermore, the groove has associated therewith a channel across and transverse to the groove disposed adjacent to the distal end of the groove but proximally of the recessed region. The channel extends more deeply into the elongated housing than the groove so as to prevent wicking of the blood toward a proximal end of the groove under a capillary tube disposed in the groove.

The blade assembly includes a beveled blade which is configured to initiate an incision in a fetal scalp with minimal force by effecting an initial penetration with the sharp tip of the blade and enlarging the incision as the blade penetration increases and a greater width of blade enters the scalp. In addition, the blade member includes a blade stopper to limit the depth to which the blade may puncture the fetal scalp.

The apparatus of the present invention may also include a light source attached thereto at the distal end of the housing, or a light source which is projected to the distal end of the housing from the proximal end thereof, optionally using a transparent or translucent housing material as a projection element or wave guide to facilitate viewing of the fetal scalp as well as back-lighting the capillary tube from the exterior of the housing.

The present invention also includes a method for collecting blood in a capillary tube from a fetal scalp, comprising advancing a fetal blood collecting apparatus into a cervix so that a distal portion thereof is located proximate the scalp of a fetus with the capillary tube on an exterior portion of the apparatus, incising the fetal scalp and causing the blood to pool at the distal end of the apparatus, viewing blood from the pool being drawn into the capillary tube and withdrawing the apparatus from the cervix after determining that a sufficient amount of blood has been drawn into the capillary tube. The method preferably but optionally includes retracting a blade employed to incise the fetal scalp after the incision is effected.

BRIEF DESCRIPTION OF THE DRAWINGS

The above advantages of the present invention will become more apparent by the following descriptions of embodiments thereof, taken in conjunction with the appended drawings, wherein:

FIG. 1 is a partial side sectional elevation of an embodiment of the present invention with a capillary tube secured thereto;

FIG. 2 is a top elevation of the embodiment of FIG. 1 with the capillary tube removed for clarity;

FIG. 2A is a distal end view of the embodiment of FIG. 2;

FIG. 3 is a top elevation of a distal portion of the apparatus of the present invention showing an alternative, preferred exterior configuration;

FIG. 3A is a distal end view of the embodiment of FIG. 3;

FIG. 4 is a schematic side elevation of a first embodiment of the invention including a light source;

FIG. 5 is a schematic side elevation of a second embodiment of the invention including a light source;

FIG. 6 is a schematic side partial sectional elevation of a third embodiment of the invention including an amnioscope having a light source associated therewith;

FIG. 7 is an enlarged view of a blade configuration suitable for use with the apparatus of the present invention; and FIG. 8 is an enlarged view of another blade configuration suitable for use with the apparatus of the present invention.

DETAILED DESCRIPTION OF THE INVENTION

Hereinafter, preferred embodiments of a fetal blood collecting apparatus of the present invention will be described in detail with reference to the appended drawings. However, the preferred embodiments are merely exemplary of the present invention, and, thus, the specific features described below are merely used to more easily describe such embodiments and to provide an overall understanding of the present invention. Accordingly, one skilled in the art will readily recognize that the present invention is not limited to the specific embodiments described below.

A first embodiment of the invention will now be described with reference to FIGS. 1, 2 and 2A of the drawings. Apparatus 10 of the present invention, which comprises an elongated element, includes an elongated housing 20, capillary tube retention element 26, biasing mechanism 30, and blade assembly 50 secured to plunger 35 of biasing mechanism 30 through extension member 54. The apparatus may optionally include a capillary tube 25 retained on elongated housing 20 by retention element 26.

The elongated housing 20 is preferably made of a polymer, and most preferably a transparent or translucent polymer, but is not limited to such materials. Elongated housing 20 includes a longitudinal bore 29 extending therethrough along longitudinal axis 15 of apparatus 10. At a distal end and on an exterior side surface 28 of the elongated housing 20 there is a groove 21 that extends longitudinally therealong parallel to longitudinal axis 15. The distal end of the groove 21 terminates at a recessed region 22 in the form of a shallow spoon or cup and the proximal end of the groove 21 terminates at end wall 24. The distal end of recessed region 22 opens into collection channel 22a, which extends to the distal end of elongated housing 20 (see FIG. 2A). The recessed region 22 may be approximately ½ cm in length (longitudinal to the housing 20) and ¼ cm in width, which is wider and slightly deeper than the groove 21. The exterior side surface 28 of elongated housing 20 also includes a transversely oriented channel 23 adjacent and across a proximal end of the recessed region 22. The channel 23 is preferably deeper than the groove 21. At a proximal end of the elongated housing 20 there are interior threads 27, which will be discussed in further detail below.

The groove 21 is sized and shaped in transverse cross section to receive a side portion of a capillary tube 25, which can be of any selected size and of a diameter small enough to draw blood thereinto by capillary action. Further, the groove 21 is formed to a predetermined length sufficient to receive the capillary tube 25. Capillary tube 25 is disposed in the groove with the distal end of the capillary tube 25 at least proximate, but preferably extending slightly into, recessed region 22 at the distal end of the groove 21. In this fashion the capillary tube 25 may be selected of any length shorter than the length of groove 21 and positioned therein on the exterior side surface 28 of elongated housing 20 by simply adjusting the longitudinal position of the capillary tube 25 so that the distal end thereof encroaches into recessed region 22. The capillary tube 25 is maintained in position partially received within the groove 21 by using a suitable retention element 26 such as a resilient band or sleeve or other suitable element known in the art.

As shown in FIG. 1, the biasing mechanism 30 includes a housing 31 that is substantially tubular, defines a plunger cavity 34 therein, and includes a first, slot-shaped opening 32 and a second, more proximally longitudinally spaced slot-shaped opening 33 extending through the side thereof to the plunger cavity 34. Within the plunger cavity 34 of biasing mechanism housing 31 there is slidably disposed a plunger 35 at its proximal end and a biasing element, preferably in the form of a coil spring 55, between plunger 35 and the distal end of housing 31. The plunger 35 is preferably formed of a hard but resilient plastic and includes a head 36 at the proximal end thereof and a cantilevered arm 37 extending longitudinally proximally from the distal end thereof, cantilevered arm 37 having first tab-shaped finger 38 and second wedge-shaped finger 39 extending laterally therefrom. The coil spring 55 is disposed between a wall 61 at the distal end of plunger cavity 34 of the biasing mechanism housing 31 and an annular shoulder 56 at the distal end of plunger 35, extension member 54 being secured at its proximal end to plunger 35 and extending distally through the coils of spring 55 and through an aperture 59 in the distal end of biasing mechanism housing 31.

With this arrangement, the distal end of coil spring 55 continually biases the plunger 35 proximally, the coil spring 55 being disposed under compression between the annular shoulder 56 and wall 61 at the distal end of plunger cavity 34. Also, the plunger 35 is redundantly kept from being displaced proximally from the biasing mechanism 30 by engagement of the first finger 38 with the proximal end of the first opening 32 and the second finger 39 with the proximal end of the second opening 33. When coil spring 55 is further compressed by distal movement of plunger 35, the plunger 35 is locked in a more distal position by the wedge-shaped second finger 39 riding distally out of second opening 33 to the inside of the plunger cavity 34 of biasing mechanism housing 31, overcoming the resiliency of arm 37 until second finger 39 is aligned with the first opening 32, upon which arm 37 biases second finger 39 outwardly.

Extension member 54 can be formed of any suitable material, but preferably comprises a metal tube or rod. As discussed above, the proximal end of the extension member 54 is secured to the plunger 35 and extends through the coil spring 55.

At the distal end of the extension member 54 is located a blade assembly 50. The blade assembly 50 includes a blade holder 53, blade stop 51 and beveled blade 52 (see FIG. 7). Alternatively, one might employ a sharp-pointed blade 52' with the point at one lateral end of the cutting edge, being more scalpel-like in configuration (see FIG. 8), mounted in a manner similar to the mounting of blade 52 to accomplish the same result. The blade holder 53 is preferably metal or plastic, but is not limited to such material, and may be formed integrally with the extension member 54. The blade holder 53 holds the beveled blade 52 in position by a set screw 57 so that the proximal end of the beveled blade 52 is secured in the blade holder 53, so that the beveled blade 52 extends longitudinally distally from the blade holder 53 through blade stop 51, which is of a suitable diameter to guide blade 52 longitudinally through the logitudinal bore 29 of elongated housing 20 with minimal lateral play. The blade stop 51 is preferably made from a polymer but can be formed from other suitable materials, and is longitudinally aligned with the blade holder 53, with beveled blade 52 extending through blade stop 51 to a predetermined distance or exposure. The beveled blade 52 is preferably an 18 gauge beveled needle tip blade, but other sizes may be employed.

When the beveled blade 52 penetrates the fetal scalp to commence an incision, the sharp tip 52a thereof requires less force to commence penetrating the scalp than with a square or rectangular blade edge oriented transverse to the direction of penetration, the remainder of the blade edge 52b to either side of the sharp tip 52a neatly laterally enlarging and opening the initial cut (enhanced by the bevel) as it penetrates the scalp at an angle. The scalpel-like blade 52' as depicted in FIG. 8 with a sharp tip 52a at one lateral end of its cutting edge and the remainder of blade edge 52b extending laterally to only one side thereof may also be employed to the same end in lieu of the central sharp-tipped beveled blade 52 illustrated in FIG. 7. While a square or rectangular blade edge will theoretically cause more bleeding (by cutting more vessels in its path) for the same depth of penetration as that of a beveled blade according to the invention, it has been demonstrated that sufficient bleeding is initiated using the beveled blade 52 according to the invention. Further, it can be appreciated that the distal end of blade stop 51 provides a limiter for controlling the depth of the incision made by the beveled blade 52. In addition, as previously noted the blade stop 51 is sized to act as a lateral support or guide to align the laterally beveled blade 52 and facilitate smooth movement thereof longitudinally within the longitudinal bore 29 of the elongated housing 20.

The elongated housing 20 is easily connected to the biasing mechanism 30 by simply inserting the blade assembly 50 and extension member 54 through the proximal end of the elongated housing 20. After full insertion to a point wherein the proximal end of elongated housing 20 abuts the distal end of biasing mechanism housing 31, an exterior thread 41 on the distal end of biasing mechanism housing 31 is rotationally engaged with the interior threads 27 at the proximal end of the elongated housing 20 until the elongated housing 20 and the biasing mechanism 30 are fully made up.

An alternative embodiment of the present invention will now be described with reference to FIGS. 3 and 3A. In particular, rather than having a groove 21 on the exterior side surface 28 of the elongated housing 20 in longitudinally parallel alignment with the elongated housing 20 as shown in FIG. 2, groove 21' is oriented at an acute angle to the longitudinal axis 15. Accordingly, when the capillary tube 25 is fitted in the groove 21', the capillary tube 25 also slants from the longitudinal axis 15 of the apparatus 10.

With this slanted groove orientation, it can be appreciated that the person collecting the blood from the fetus gains a three-dimensional visualization of the capillary tube 25 when looking down elongated housing 20 along longitudinal axis 15. This perspective allows the person taking the blood sample to visually ascertain when a sufficient amount of blood has been collected. Therefore, in this alternative embodiment, visualization is enhanced not only because the capillary tube 25 is located on the exterior side surface 28 of the elongated housing 20 (as in the previously discussed embodiment), but also because the capillary tube 25 is slanted off-axis due to the orientation of groove 21' to provide a three-dimensional view of the capillary tube 25. It should also be noted that recessed region 22 at the distal end of slanted groove 21' opens directly onto the distal end of elongated housing 20 rather than through a channel 22a.

Another alternative embodiment of the present invention will now be described with reference to FIG. 4, which is a schematic representation of apparatus 10. In this embodiment, a power source 70 such as a minute battery is operably coupled to a directional light source 71 located on the exterior side surface 28 of elongated housing 20 of the apparatus 10. As shown, the light source 71 may be located near the proximal end of the elongated housing 20 or near the distal end, for example, immediately proximal of the location of capillary tube 25. The light is directed toward the distal end of the elongated housing 20. This configuration and orientation of light source 71 further facilitates visualization of the fetal scalp and filling of the capillary tube 25 for prompt and accurate determination of when a sufficient amount of blood has been collected. The light source 71 may be used in the apparatus 10 with a groove 21 that is longitudinally aligned with the longitudinal axis 15 of the apparatus 10, or the apparatus 10 with the groove 21' that is slanted thereto. An alternative apparatus light source design is depicted in FIG. 5, wherein a power source 70 and light source 71' are located toward the proximal end of apparatus 10 and the material of the elongated housing 20, formed with beneficial light transmission characteristics, is employed as a fiber optic-type wave guide to conduct light to the distal end of the apparatus 10 and to back-light the capillary tube 25 from the exterior side surface 28 of the elongated housing 20. In this embodiment, either the entirety of elongated housing 20 or a portion 20a thereof extending, for example, to the distal end thereof and under at least a portion of groove 21 or 21' may be formed of the light-guiding material. Finally, in either embodiment, a chemical reaction of the type used in so-called "light sticks" for emergency use or amusement may be employed as a light source 71 or 71' as known in the art, eliminating the need for a separate power source. As yet another alternative and as depicted schematically in FIG. 6, a light source 71 (and, as required, a power source 70) may be included on the interior of amnioscope 60, aimed toward the narrow end thereof, or provided with the remainder of apparatus 10 and includes a clip 73 for affixation thereof to amnioscope 60. If desired, an optical fiber 75 may be extended from light source 71 to a location near the distal end of amnioscope 60 to light the fetal scalp and capillary tube 25 from above.

The present invention is thus shown to provide a simple, reliable and robust apparatus for collection of a fetal scalp blood sample. The apparatus 10 of the present invention, in any of its embodiments or variations thereof, is suitable for fabrication as a single-use, or disposable, product provided to the user in sterile form enclosed in a protective cover, such as a sealed, transparent polymer bag. However, the invention is not limited to disposable devices, and may be fabricated from components suitable for either single or repeated use.

A method for using the present invention will now be described with reference to the drawings. A cone-shaped amnioscope 60 (see FIG. 6) is advanced in the cervix until its end rests upon a fetal scalp FS. The apparatus 10 of the present invention, comprising an elongated housing 20 bearing a capillary tube 25 retained thereon proximate the distal end thereof in groove 21 or 21' by retention element 26, is then inserted into the amnioscope 60 until its distal end rests on the scalp. The head 36 of the plunger 35 is then depressed distally by the user until the second finger 39 is engaged with the first opening 32, which in turn extends the beveled blade 52 beyond the distal end of the elongated housing 20. As the beveled blade 52 extends beyond the distal end of elongated housing 20, it incises the fetal scalp until the distal end of blade stop 51 is flush with the fetal scalp. Thus, both the blade stop 51 and the distal end of the elongated housing 20 provide protection against excessive penetration of the blade puncturing the fetal scalp. Beveled blade 52 is then retracted from the fetal scalp by simply depressing the first finger 38 into the first opening 32, causing the second finger 39 to depress and exit the first opening 32 proximally and quickly enter into the second opening 33 under bias of coil spring 55. After the blade 52 has been retracted from the fetal scalp, apparatus 10 may be moved so that the portion of the distal end of elongated housing 20 whereon recessed region 22 is located is immediately below the incision in the fetal scalp so that blood pools in the recessed region 22 proximate the location of the distal end of capillary tube 25. Pooled blood is then drawn into the capillary tube 25 by capillary action. Proximal movement, as by wicking, of blood within groove 21 or 21' under capillary tube 25 is inhibited by the presence of transversely-oriented channel 23. Since the capillary tube 25 is located on an upper portion of the exterior side surface 28 of the elongated housing 20, the capillary tube 25 is easily viewed by the person collecting the blood. Further, when the blood begins to be drawn into the capillary tube 25, due to its placement on the exterior of apparatus 10, there are no visual obstructions surrounding the capillary tube 25. Thus, a person collecting the blood can easily determine when the capillary tube 25 has drawn a sufficient sample of blood for analysis. After visually confirming that the capillary tube has drawn sufficient blood therein, the apparatus 10 is withdrawn from the fetal scalp and the capillary tube 25 is easily removed from groove 21 or 21' on the exterior side surface 28 of the elongated housing 20 without fear of damage or contamination of capillary tube 25 or the blood sample therein due to the resiliency of retention element 26. If needed, another capillary tube 25 may be then easily mounted in groove 21 or 21', retained in appropriate position by retention element 26 and inserted on apparatus 10 to fill that capillary tube 25 with blood.

The previous description of the preferred embodiments is provided to enable a person of ordinary skill in the art to make or use the present invention. Moreover, various additions, deletions and modifications to these embodiments will be readily apparent to those of such ordinary skill without departing from the scope of the invention as defined by the claims.

What is claimed is:

1. A fetal blood collection apparatus, comprising:
    an elongated housing having a proximal end, a distal end and a bore extending longitudinally therethrough;
    a biasing mechanism configured to provide a proximal longitudinal bias to a member carried by the elongated housing;
    a blade located at the distal end of the elongated housing within the bore thereof and extendable distally therefrom, the blade operably connected to the biasing mechanism through the member; and
    a longitudinally extending groove in an exterior side surface of the elongated housing proximate a distal end thereof, the groove configured for receiving at least a portion of a capillary tube therein.

2. The apparatus of claim 1, further comprising a recessed region on the exterior side surface of the elongated housing proximate a distal end of the groove.

3. The apparatus of claim 2, wherein the groove is formed to a predetermined length so that a capillary tube of any length shorter than the length of the groove may be positioned in the groove with a distal end of the capillary tube disposed adjacent to the recessed region.

4. The apparatus of claim 2, further comprising a channel on the exterior side surface of the elongated housing disposed across, and oriented substantially transverse to, the groove at a location proximal of the recessed region.

5. The apparatus of claim 4, wherein said channel extends to a greater depth in the exterior side surface of the elongated housing than a depth of the groove.

6. The apparatus of claim 1, further comprising a capillary tube retention element located on the elongated housing within a longitudinal extent of the groove.

7. The apparatus of claim 6, wherein the capillary tube retention element comprises a resilient annular element.

8. The apparatus of claim 1, wherein said blade is configured with a cutting edge disposed in nonperpendicular relationship to the direction of the longitudinal bias.

9. The apparatus of claim 8, wherein the cutting edge comprises a beveled cutting edge.

10. The apparatus of claim 9, wherein the beveled cutting edge terminates distally at a sharp point.

11. The apparatus of claim 1, further comprising a stop element for limiting distal longitudinal exposure of the blade.

12. The apparatus of claim 1, wherein said biasing mechanism further comprises a spring and the member comprises a plunger including a head protruding proximally of the apparatus, and the apparatus further includes a releasable catch configured to cooperatively engage another element of the apparatus to maintain the plunger in a relatively distal position with the blade extending distally from the elongated housing against a bias of the spring.

13. The apparatus of claim 1, wherein the groove is oriented substantially parallel to a longitudinal axis of the distal end of the elongated housing.

14. The apparatus of claim 1, wherein the groove is oriented in nonparallel relationship to a longitudinal axis of the distal end of the elongated housing.

15. The apparatus of claim 1, further comprising a light source configured to illuminate an area proximate the distal end of the elongated housing.

16. The apparatus of claim 15, further including an electrical power source for the light source.

17. The apparatus of claim 15, wherein the light source is aimed toward the distal end of the elongated housing.

18. The apparatus of claim 15, wherein at least a portion of the elongated housing is formed of a material to provide a light guide from the light source to the distal end of the elongated housing.

19. The apparatus of claim 18, wherein an area of the exterior side surface of the elongated housing in a region underlying at least a portion of the groove is formed of the material.

20. The apparatus of claim 19, wherein substantially an entire distal portion of the elongated housing from the distal end thereof to a proximal end of the groove is formed of the material.

21. The apparatus of claim 15, wherein the light source is mountable to an amnioscope.

22. The apparatus of claim 1, wherein the blade is operably connected to the biasing mechanism member through at least one intermediate member extending into the bore of the elongated housing.

23. A method for collecting blood from a fetal scalp, comprising:

advancing an elongated element internally carrying a blade at a distal end thereof into a cervix to a location proximate a scalp surface of a fetus;

extending the blade against a spring bias from the distal end of the elongated element;

making an incision in the scalp surface to a limited depth with the extended blade;

retracting the blade within the elongated element using the spring bias;

collecting blood emanating from the incision on a region of an exterior surface of the elongated element;

drawing blood collected on the region of the exterior surface by capillary action into a distal end of a capillary tube secured to the exterior surface of the elongated element; and withdrawing the elongated element from the cervix.

24. The method of claim 23, further comprising illuminating an area surrounding the distal end of the elongated element with a light source carried by the elongated element.

25. The method of claim 23, further comprising resiliently securing the capillary tube to the exterior surface of the elongated element prior to advancing the elongated element into the cervix.

26. The method of claim 23, further comprising securing the capillary tube to the exterior surface of the elongated element in nonparallel orientation to a longitudinal axis thereof prior to advancing the elongated element into the cervix.

27. The method of claim 23, further comprising securing the capillary tube at least partially within a groove on the exterior surface of the elongated element.

28. The method of claim 27, further comprising collecting the blood emanating from the incision in a recessed region on a distal end of the exterior surface proximate a distal end of the groove.

29. The method of claim 28, further comprising substantially constraining proximal movement of blood collected in the recessed region in the groove under the capillary tube during the drawing of the blood thereinto.

30. The method of claim 23, further comprising extending the blade from the distal end of the elongated element prior to making the incision and withdrawing the blade into the distal end of the elongated element prior to collecting the blood emanating from the incision.

31. The method of claim 23, further comprising initiating the incision by point contact of a sharp, distal tip of the blade and enlarging the incision laterally from the point contact.

* * * * *

UNITED STATES PATENT AND TRADEMARK OFFICE
CERTIFICATE OF CORRECTION

PATENT NO. : 6,423,011 B1
DATED : July 23, 2002
INVENTOR(S) : Sabaratnam Arulkumaran and Wm. Dean Wallace It is certified that error appears in the above-identified patent and that said Letters Patent is hereby corrected as shown below:

Column 4,
Line 39, change "will be discussed in further detail below" to -- receive an externally threaded distal portion of housing 31, the structure of which is discussed in detail below --

Column 5,
Line 49, change "logitudinal" to -- longitudinal --

Column 6,
Line 11, change "noted" to -- noted --

Column 10,
Lines 40-44, delete the entirety of claim 30.

Signed and Sealed this

Thirteenth Day of April, 2004

JON W. DUDAS
*Acting Director of the United States Patent and Trademark Office*